United States Patent [19]

Strandberg, Jr. et al.

[11] 4,399,403

[45] Aug. 16, 1983

[54] MICROWAVE MOISTURE MEASURING, INDICATING AND CONTROL APPARATUS

[75] Inventors: Charles F. Strandberg, Jr., High Point; Robert C. Strandberg, Greensboro, both of N.C.

[73] Assignee: Strandberg Engineering Laboratories, Inc., Greensboro, N.C.

[21] Appl. No.: 304,580

[22] Filed: Sep. 22, 1981

[51] Int. Cl.³ ............................................ G01R 27/04
[52] U.S. Cl. ............................................ 324/58.5 A
[58] Field of Search ...................... 324/58.5 A, 58.5 B, 324/58.5 R

[56] References Cited

U.S. PATENT DOCUMENTS

| | | | |
|---|---|---|---|
| 2,142,648 | 1/1939 | Linder | 324/58.5 A X |
| 2,165,214 | 7/1939 | Blau et al. | 324/58.5 A |
| 2,212,211 | 8/1940 | Pfund | 324/58.5 A X |
| 2,670,649 | 3/1954 | Robinson | 324/58.5 A X |
| 3,534,260 | 10/1970 | Walker | 324/58.5 A |
| 3,639,834 | 2/1972 | Walker | 324/58.5 B |
| 3,913,012 | 10/1975 | Kujath | 324/58.5 A |
| 4,156,843 | 5/1979 | Strandberg, Jr. et al. | 324/58.5 B |

FOREIGN PATENT DOCUMENTS

| | | | |
|---|---|---|---|
| 1052250 | 12/1966 | United Kingdom | 324/58.5 B |
| 559192 | 7/1977 | U.S.S.R. | 324/58.5 A |

*Primary Examiner*—Stanley T. Krawczewicz

*Attorney, Agent, or Firm*—Munson H. Lane, Jr.

[57] ABSTRACT

A microwave moisture measuring, indicating and control apparatus for measuring the moisture content of material in an inspection area, comprising a microwave transmitting transducer including a modulated signal microwave generator and parabolic reflector for directing a beam of microwave energy through the inspection area and the material to be monitored therein and including a microwave absorping material layer in the path of the microwave beam directed from the reflector toward the inspection area. A microwave receiver transducer is located on the opposite side of the inspection area from the transmitting transducer and also includes a parabolic reflector for receiving the microwave energy monitoring beam after its passage through the inspection area and direct from the same to a microwave detector, the monitoring beam also passing through a layer of microwave absorbing material at the receiver transducer. The microwave detector produces an output signal which is processed by moisture measuring and indicating circuitry to provide an output reading which is directly proportional to the amount of moisture present in the material located in the inspection area. The device further includes a moisture control circuit for providing correctional control signals for restoring the moisture content of the material to a selected level, if desired.

9 Claims, 5 Drawing Figures

MICROWAVE MOISTURE MEASURING, INDICATING AND CONTROL APPARATUS

BACKGROUND AND OBJECTS OF THE INVENTION

The present invention relates in general to microwave moisture indicator and control apparatus, and more particularly to an improved microwave moisture indicator and control device of the transmission type having a pair of microwave transducers for indicating moisture levels of moving webs or material transported thereon, conveyorized items, flowing liquid in conduit systems, or stationary bulk materials such as powdered or granular samples, and producing an output indication of the moisture content of the material or items in the microwave transmission path.

Heretofore, various microwave moisture measuring devices have been disclosed, wherein microwave energy is directed through sheet material and measurements made of attenuation of the microwave energy transmitted through the web to indicate moisture content. Examples of these are found in U.S. Pat. Nos. 3,534,260, 3,639,834 and 3,913,012. Since microwave energy absorbtivity varies only slightly with variations in web moisture content, large differences in moisture produced only slight differences in absorption, so that accurate measurement is difficult to attain with such devices. Efforts to overcome problems of accuracy in such devices have led to the reflective microwave energy moisture measuring devices shown in British Pat. No. 1,052,250 and our earlier U.S. Pat. No. 4,156,843.

An object of the present invention is the provision of an improved novel microwave moisture indicator and control apparatus having a pair of spaced apart microwave transducers using parabolic reflectors to permit moisture in a large area of a web, conveyor path, or body of material to be sensed, whereby variations in moisture across the area being monitored are largely canceled out and more nearly average moisture values are measureable than would occur by conventional reflectance or transmission microwave moisture measuring system.

The importance of being able to make reliable moisture measurements on moving webs or sheets of material moving along a conveyance path, such as warp or other fabric webs, in numerous textile industry applications, has been described in our above identified earlier U.S. Pat. No. 4,156,843, disclosing a reflectance type microwave moisture indicator and control device, and the transmission type microwave moisture indicator apparatus of the present invention is equally suitable for those applications. Additionally, the present invention is designed for a broad range of microwave moisture measurements on any other hygroscopic web material, or to make microwave measurements in the food processing field for measuring the moisture content of food products on conveyors, such as moving conveyors of a non-interfering material like rubber, or moving through chutes or collected in hoppers, and may also be used to detect contaminating moisture in anhydrous liquid flowing through plastic pipe or similar conveyance systems. Moisture content of web-like materials such as wooden boards, veneers, and other webs of variable density may also be advantageously measured and indicated by the large area transmission type microwave moisture indicator and control apparatus of the present invention.

SUMMARY OF THE INVENTION

The present microwave moisture indicator apparatus, to achieve the large area moisture sensing, utilizes a mircowave transmitter transducer and a microwave receiver transducer having parabolic reflectors which face each other over a distance up to several feet, with the microwave transmitter and receiver antennas of the transducers positioned at the focal points of the parabolic reflectors so that they radiate and receive toward the reflectors only and are insensitive from their sides which face the material being sensed. Thus, all energy transferred must reflect first off of the reflector at the transmitter and then off the reflector at the receiver to finally reach the receiver antenna. By using comparatively large reflectors, such for example as reflectors about 18 inches in diameter, the moisture in a large area of the web is sensed. This offers distinctive advantages in making moisture measurements on moving textile webs, wooden boards, veneers and other webs of variable density in which the moisture may be variable across the profile. This variation in moisture is due to either or both variable density of the web or inconsistent moisture application and/or drying in the process. The large area sensing arrangement produces a more nearly average value moisture reading.

Other objects, advantages and capabilities of the present invention will become apparent from the following detailed description, taken in conjunction with the accompanying drawings illustrating a perfered embodiment of the invention.

DETAILED DESCRIPTION OF A PREFERRED EMBODIMENT

Figure 1:
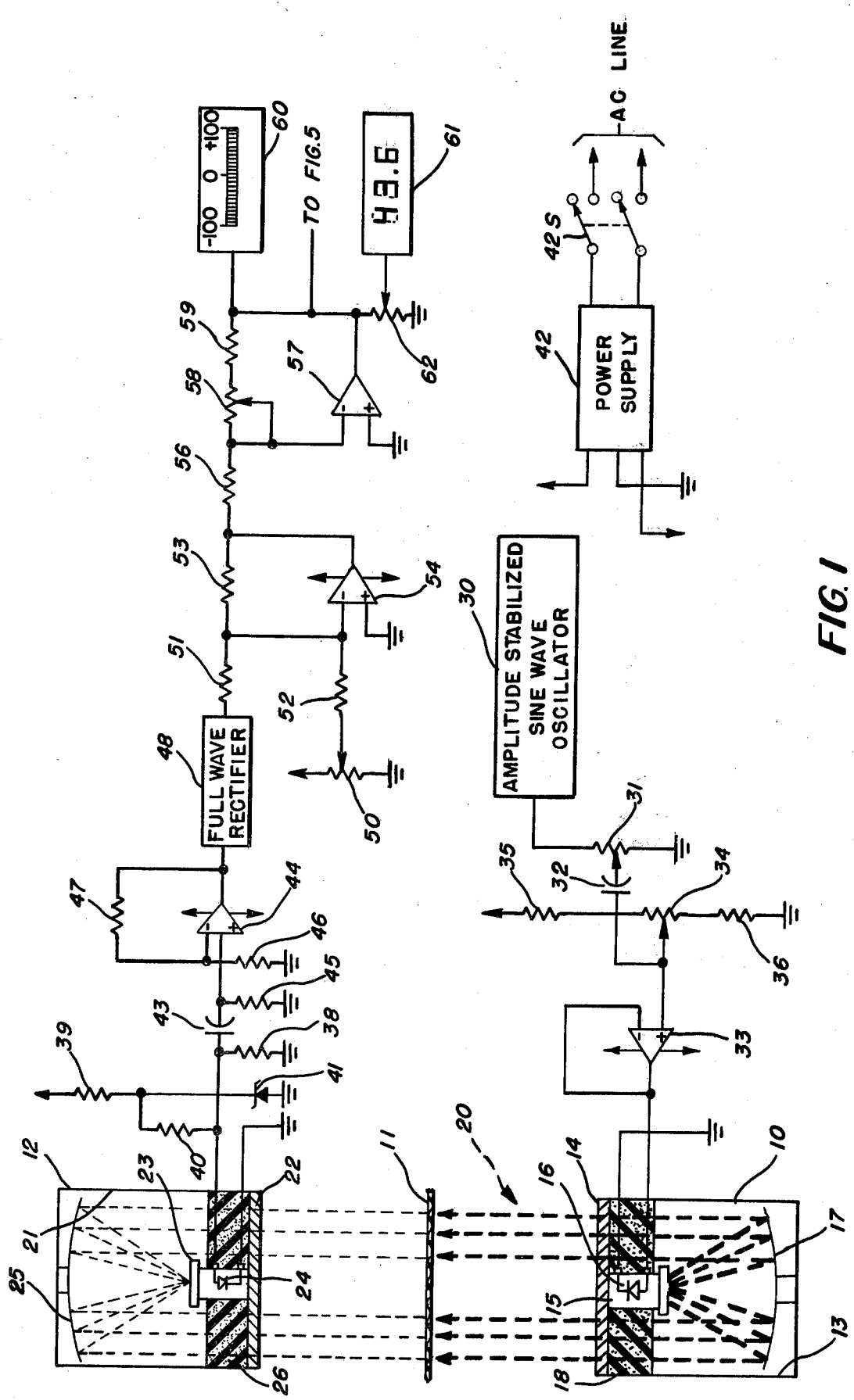
FIG. 1 is a partial block diagram and partial schematic diagram of a microwave moisture measuring and indicating portion and circuit of the transmission type, embodying the present invention.
Figure 2:
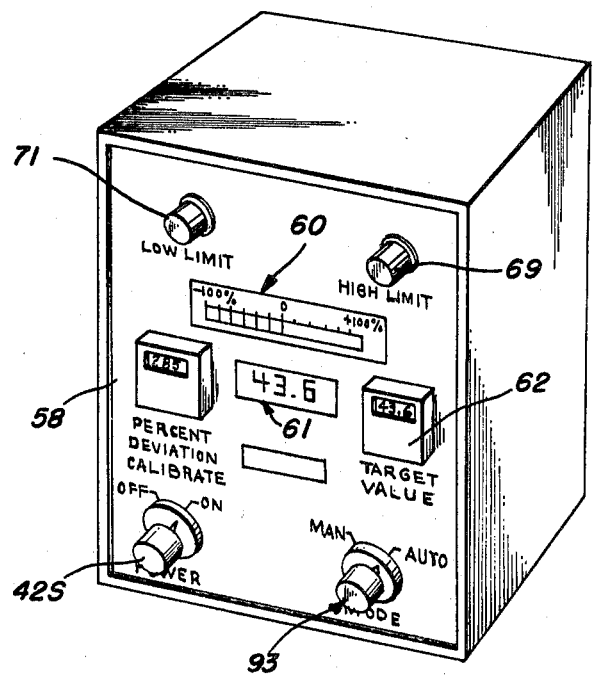
FIG. 2 is a prespective view of the indicating and control unit cabinet for the moisture indicator and control apparatus of the present invention.
Figure 4:
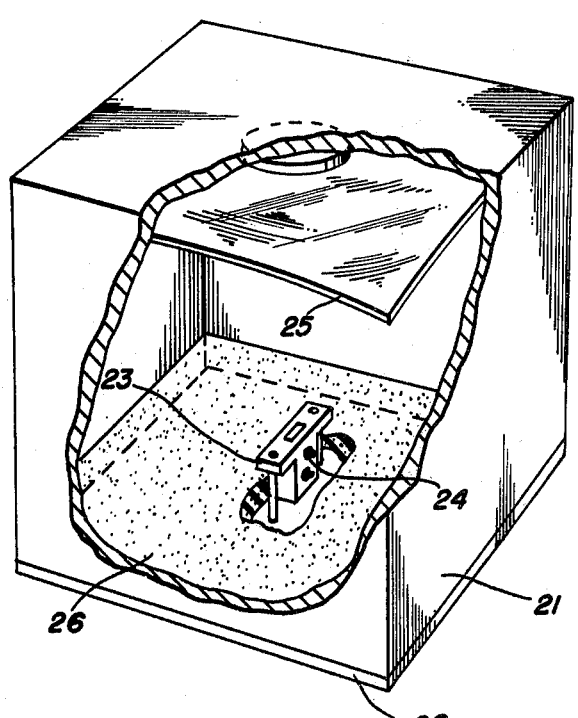
FIG. 4 is a cut-a-way perspective view of the microwave receiver transducer unit of the present invention.

Referring to the drawings, wherein like reference characters designate corresponding parts throughout the several figures, the microwave moisture detection components of the moisture indicator and control transmission type apparatus comprise a microwave transmitter transducer indicated by the reference character 10, shown positioned beneath a moving web 11 of material whose moisture content is being monitored, and a microwave receiver transducer 12 positioned above the moving web 11 in substantial vertical alignment with the microwave transmitter transducer 10. While this embodiment is described in conjunction with an application wherein the moisture content of a moving hygroscopic web of material is being monitored, it will be understood that the invention is equally applicable to monitoring of many different types of conveyorized materials or products, such as food products on moving conveyors of non-interferring material, such as rubber, or to moving web-like materials such as wooden boards, veneers, or webs of any other material in which moisture may vary across the width of the web, and will also be applicable to moisture content monitoring of stationary bodies of materials, for example granular, powdered or comminuted masses of stationary bulk material.

Figure 3:
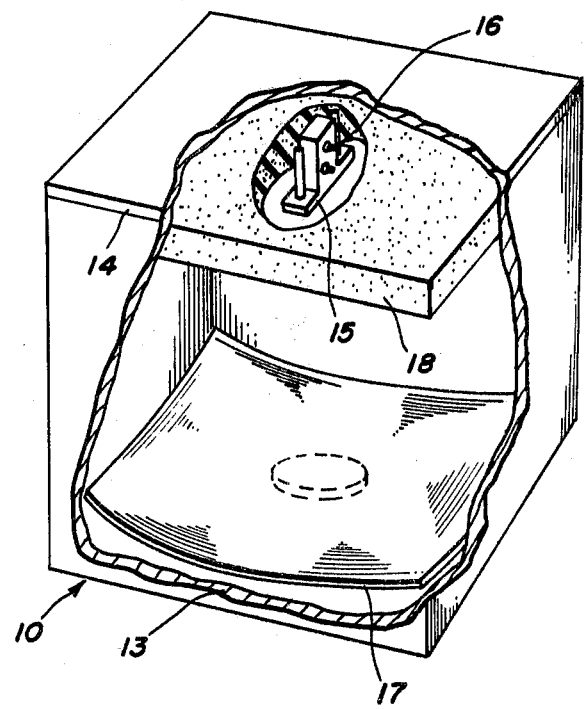
FIG. 3 is a cut-a-way perspective view of the microwave transmitter transducer unit.

The microwave transmitter transducer 10 is housed in a boxed enclosure or cabinet 13 having a low dielectric plate or window 14 to protect the transducer from hostile environments while allowing non-attenuated transmission of the microwave radiation therethrough. An X-band Gunn oscillator 15 with its integral Gunn diode 16 is mounted to the low dielectric plate 14 with the transmitting end of the Gunn oscillator 15 aimed downwardly toward a parabolic reflector 17 supported in the lower portion of the box-like enclosure or cabinet 13 and located at the focal length of the reflector 17 from the opening in the Gunn oscillator 15. In one satisfactory example, the wave length of the X-band microwave energy is three centimeters, which corresponds to a frequency of 10 gigahertz or 10,000 megahertz, and the parabolic reflector 17 in this example is a comparatively large reflector, for example about 18 inches in diameter. A layer of microwave absorbing material, indicated at 18 in FIGS. 1 and 3, is mounted to the dielectric plate or window 14 immediately underlying the plate 14, to reduce the effect of standing waves between the transducers and provide isolation for the Gunn oscillator. The material may be one of the commercially available X-band microwave attenuating materials, such as foamed plastic formed of polyurethane containing a lossy conductive ingredient such as graphite, or may be formed of a sheet of about one inch thickness of the material marketed under the name Eccosorb H by Emerson & Cummings, Inc.

The microwave radiation emitted by the Gunn oscillator 15 strikes the parabolic reflector 17 after spreading out to a convenient width and is reflected back through the microwave absorping material 18 and low dielectric plate 14 and directed as a microwave radiation beam, indicated by reference character 20 against the moving web 11 of material to be monitored where it is partially attenuated by the moisture contained in the moving web 11.

The microwave receiver transducer 12 is similar in construction to the transmitter transducer 10, as it includes a box like enclosure or cabinet 21 having a low dielectric plate or window 22 extending across the lower end of the receiver transducer housing 21 to protect the transducer from hostile environment, and includes an X-band detector 23, for example of the type having an integral Schottky dioide 24, aimed upwardly toward a parabolic reflector 25 supported in the upper end portion of the receiver enclosure 21 and located at the focal length of the X-band detector 23. Thus the attenuated radiation in the microwave energy beam 20, which exits from the upper surface of the moving web 11, enters the microwave receiver transducer 12, located above the moving web, by passing through the low dielectric plate or window 22 and a layer of microwave absorping material 26, like the microwave absorping material 18 of the transmitter transducer 10, and strikes the parabolic reflector 25 where it is focused on to the opening of the X-band detector 23. The microwave radiation thus detected by the X-band detector 23 is inversely proportional to the degree of attenuation due to the moisture present in the moving web 11.

Referring to the partial block diagram and partial schematic diagram of the measuring and indicating circuitry shown in FIG. 1, a conventional amplitude-stabilized sine-wave oscillator 30 provides the modulation source for the transmitting Gunn oscillator 15. The oscillator frequency is not critical and only serves as a more easily recoverable signal than the 10.525 GH$_z$ signal transmitted by the X-band oscillator 15. In practice, 10,000 megaHertz was chosen as a suitable frequency. The modulation level potentiometer 31 connected to the oscillator 30 allows precise adjustment of the sine-wave amplitude which is coupled via capacitor 32 to the input of a voltage-follower buffer 33. The X-band Gunn oscillator 15 requires a D-C bias voltage to operate. The D-C bias potentiometer 34 and resistors 35 and 36 provide means to set this bias precisely.

After the modulated microwave signal in the monitoring beam 20 reaches the X-band detector 23, it is detected by the Schottky diode 24 and the signal thus appearing across resistor 38 is a 10K H$_z$ sine-wave inversely proportional to the amount of moisture present in the web 11. A D-C bias current of approximately 32 microamperes is required by the Schottky diode 24. Resistors 39, 40, and 38 along with zener diode 41, form a regulated supply to furnish the required bias current from the power supply 42. The detected signal is next coupled via capacitor 43 to the plus (+) input of operational amplifier 44. Resistor 45 serves as an input load resistor for the amplifier. Amplifier gain is controlled by resistors 46 and 47.

The signal conversion from A-C to D-C is accomplished by the full wave rectifier 48. This is a precision operational amplifier-based converter of standard design, wherein the D-C output voltage is negative and is equal to the average value of the A-C input voltage. In the case of no moisture in the web 11 between the transducers 10 and 12, the output of the full-wave rectifier 48 is maximum (most negative). As the moisture increases, the output of the rectifier 48 becomes less negative.

The zero potentiometer 50, along with resistors 51, 52, and 53 and amplifier 54 provides a convenient means of obtaining a zero voltage signal for zero moisture. Amplifier 54 is connected in the inverting mode as a summing amplifier. With the minus (−) input of amplifier 54 a virtual ground, the setting of the zero potentiometer 50 can be adjusted so that the positive current through resistor 52 is equal to the negative current through resistor 51. At this point the voltage output of amplifier 54 is zero. Resistor 53 provides the necessary gain for the stage. Therefore, the voltage output of amplifier 54 can be set to zero volts at zero moisture and will become increasingly more negative with increasing moisture. This is due to the reduction in the negative output of the full-wave rectifier 48 with increasing moisture.

The output of amplifier 34 is connected through resistor 56 to the minus (−) input of amplifier 57. This amplifier is connected in the inverting mode with the percent deviation calibrate potentiometer 58 and resistor 59 forming the gain feedback resistance. The output of this amplifier 57 is inverted from that of amplifier 34. It is also zero volts at zero moisture but becomes increasingly positive with increasing moisture. The output of amplifier 57 is connected to a standard bar-graph or edge-type voltmeter 60, to display in analog form the output of the amplifier 57 from zero (0) volts to plus (+)

2 volts corresponding to a full scale calibration from −100% to +100%, and thus an indication of the moisture present in the web. A digital readout in the form of a 3-digit voltmeter 61 is also connected, via the target value potentiometer 62, to the output of amplifier 57. This is used to display the actual moisture content in the web. The range of this voltmeter 61 is zero (0) to plus (+) 0.999 volts full scale.

When the microwave moisture indicator and controller is installed, the percent deviation display 60 and the digital readout 61 are calibrated in the following manner: With no web between the transducers, the zero potentiometer 50 is set to produce a zero voltage output at the output of amplifier 57. This is easily achieved and is equivalent to a −100% (0 volts) reading on the bar-graph percent deviation display 60. Next, the moisture bearing web 11 is introduced between the transducers 11, 12. With the actual moisture in the web known and separately verified by some other measurement means, the percent deviation calibrate potentiometer 58 is next set to cause the percent deviation bar-graph display 60 to read mid-scale or 0% deviation. This corresponds to a plus (+) 1 volt output from amplifier 57. The target value potentiometer 62, connected to the output of amplifier 57, is equipped with a suitable readout scale such as a digital turns-counting dial. This allows the potentiometer to be set and its position read accurately. At this point, with the output of amplifier 57 at plus (+) 1 volt, the target value potentiometer 62 is set to the value of the actual moisture in the web, such as 43.6 or 43.6% of the adjustable range of the potentiometer. The digital readout will display this value also as 43.6% (actually 0.436 volts). Both displays will now track true variations in moisture content from 0% moisture content (−100% deviation) to a maximum of 87.2% moisture content (+100% deviation). It is evident that any other values can also be calibrated and displayed. To facilitate accurate recalibrations, the percent deviation calibrate potentiometer is also equipped with a turns-counting dial.

Figure 5:
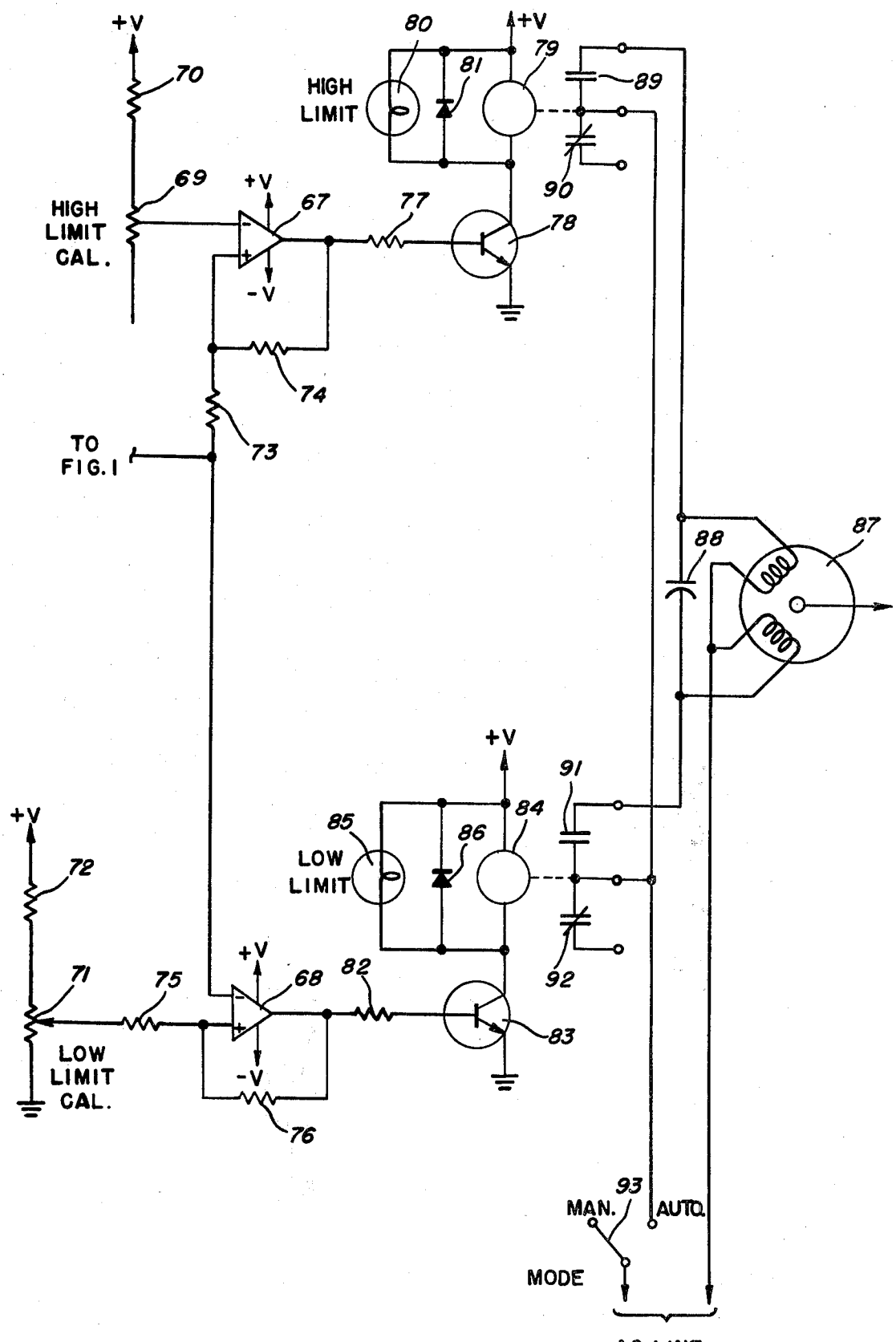
FIG. 5 is a schematic diagram of the moisture control circuit portion of the invention to be used with the circuit of FIG. 1.

The output of amplifier 57 also furnishes the required signal for the controlling portion of the instrument shown in FIG. 5. This signal is fed to two comparators 67 and 68. At the high limit comparator 67, the signal is applied, via resistor 73 to the + input. Resistors 73 and 74 provide slight hysteresis for the comparator. The high limit calibration (High Limit Cal.) potentiometer 69 and series resistor 70 provide means for setting a voltage, proportional to a point on the meter scale 60, above which control action is desired. When the voltage at the + input of comparator 67 exceeds the voltage at the − input, the output of the comparator goes high, thereby energizing transistor 78 via base current-limiting resistor 77. This, in turn, grounds the lower side of relay coil 79, lamp 80, and the anode of diode 81 causing the lamp to give a visual indication that the limit was exceeded and energizing the relay. The normally open contacts 89 make and voltage is applied to one winding of the two-coil reversible control motor 87 if the Mode switch 93 is positioned to Auto.

Operation of the low limit comparator 68 is similar, except that the inputs to the comparator are reversed. This results in operation of relay 84 and lamp 85 when the reading on the meter falls below the value set on the low limit calibration (Low Limit Cal.) potentiometer 71. Resistors 75 and 76 provide hysteresis for this comparator in like manner of resistors 73 and 74.

Diodes 81 and 86 provide return paths for the inductive relay coil discharges when either transistor 78 or 83 turns off. Capacitor 88 provides the required phase shift for the control motor 87. The entire unit is powered by a conventional dual regulated power supply 42, via a power, off-on switch 42s from standard A-C supply lines.

What is claimed:

1. A microwave moisture measuring and indicating apparatus for measuring the moisture content of moisture absorping material in an inspection area comprising a microwave transmitter means located to one side of the inspection area for transmitting a microwave monitoring beam of a selected frequency and energy level toward and through the material at the inspection area, a microwave receiver means located to the opposite side of the inspection area for receiving microwaves transmitted through the inspection area and the material located therein, said microwave transmitter means including a concave substantially parabolic reflector facing toward the inspection area and a microwave oscillator means providing a localized source of microwave energy spaced toward the inspection area from said parabolic reflector and located substantially at the focal point of the latter for directing microwave energy toward said parabolic reflector which is thereupon reflected toward the inspection area as a microwave monitoring beam of much larger transverse area than said source, said microwave receiver means including a substantially parabolic receiver reflector similar in size and shape to the reflector of said transmitter means located in the path of said monitoring beam to receive microwave energy after passage through said inspection area and including a microwave detector means located toward said inspection area from said parabolic receiver reflector at substantially the focal point thereof for detecting the microwave energy impinging on said parabolic receiver reflector and reflected thereby to said detector means and producing a detector output signal, signal processing means for amplifying and processing said detector output signal for producing a D-C moisture indicating signal which is directly proportional to the moisture content of the material in said inspection area through which the microwave energy of said beam passed, indicator means responsive to said D-C moisture indicating signal for indicating a quantity which is a function of the moisture content of said material, and each of said microwave transmitter means and microwave receiver means having a layer of microwave absorbing material between the respective parabolic reflectors and said inspection zone in the path of the microwave energy forming said monitoring beam.

2. A microwave moisture measuring and indicating apparatus as defined in claim 1, wherein said parabolic reflectors are of a size producing a monitoring beam of greater than one foot in cross-sectional width in all transverse directions.

3. A microwave moisture measuring and indicating apparatus as defined in claim 1, wherein said parabolic reflectors are of a size producing a monitoring beam is at least about 18 inches in cross-sectional width in all transverse directions.

4. A microwave moisture measuring and indicating apparatus as defined in claim 1, wherein said signal processing means includes an adjustable beam amplifier means for amplifying the output signal from said detector means, a signal conversion means for converting the amplified output signal to a D-C output signal which is substantially equal to the average value of the signal input to the conversion means, zero off-setting means for off-setting the signal detected by said detector means when no material is interposed in the transmitted beam at said inspection area, said zero setting means being adjustable to produce a D-C output signal equal to and of opposite polarity to the signal produced by said signal conversion means when no material is located in said inspection area, inverter amplifier means having a summing input node for summing the output signals of said conversion means and said off-setting means and for amplifying the summation signal and producing said D-C moisture indicating signal.

5. A microwave moisture measuring and indicating apparatus as defined in claim 2, wherein said signal processing means includes an adjustable beam amplifier means for amplifying the output signal from said detector means, a signal conversion means for converting the amplified output signal to a D-C output signal which is substantially equal to the average value of the signal input to the conversion means, zero off-setting means for off-setting the signal detected by said detector means when no material is interposed in the transmitted beam at said inspection area, said zero setting means being adjustable to produce a D-C output signal equal to and of opposite polarity to the signal produced by said signal conversion means when no material is located in said inspection area, inverter amplifier means having a summing input mode for summing the output signals of said conversion means and said off-setting means and for amplifying the summation signal and producing said D-C moisture indicating signal.

6. A microwave moisture measuring and indicating apparatus as defined in claim 1, wherein said transmitter means includes an X-band transmitting oscillator forming said microwave energy source, an amplitude-stabilized sign-wave oscillator providing an A-C modulation source for said X-band transmitting oscillator, and modulation level adjusting means for adjusting the sign-wave amplitude of the modulation signal supplied by said A-C modulation source to said X-band transmitting oscillator.

7. A microwave moisture measuring and indicating apparatus as defined in claim 6, wherein said X-band transmitting oscillator is an X-band Gunn oscillator having an integral Gunn diode.

8. A microwave moisture measuring and indicating apparatus as defined in either of claims 2, 4 or 5, wherein said transmitter means includes an X-band transmitting oscillator forming said microwave energy source, an amplitude-stabilized sign-wave oscillator providing an A-C modulation source for said X-band transmitting oscillator, and modulation level adjusting means for adjusting the sign-wave amplitude of the modulation signal supplied by said A-C modulation source to said X-band transmitting oscillator.

9. A microwave moisture measuring and indicating apparatus as defined in either of claims 1, 2, 4 or 6, wherein each of said microwave transmitter means and said microwave receiver means are in the form of a box-like cabinet housing the respective parabolic reflector in the distal end portion of said cabinet relative to said inspection area and having the respective microwave energy oscillator source and detector means and the respective microwave absorbing material layer located in the proximal end portion of the respective cabinet relative to the inspection zone, each cabinet having a low dielectric microwave transmitting window covering the proximal end of the cabinet nearest the inspection zone and disposed immediately adjacent said microwave absorbing material layer.

* * * * *